(12) United States Patent
Gainor

(10) Patent No.: US 9,486,314 B2
(45) Date of Patent: Nov. 8, 2016

(54) LOW-PROFILE PROSTHETIC VALVE STRUCTURE

(71) Applicant: HLT, Inc., Maple Grove, MN (US)

(72) Inventor: John P. Gainor, Mendota Heights, MN (US)

(73) Assignee: HLT, Inc., Maple Grove, MN (US)

( * ) Notice: Subject to any disclaimer, the term of this patent is extended or adjusted under 35 U.S.C. 154(b) by 153 days.

(21) Appl. No.: 14/212,442

(22) Filed: Mar. 14, 2014

(65) Prior Publication Data

US 2014/0288639 A1    Sep. 25, 2014

Related U.S. Application Data

(60) Provisional application No. 61/800,153, filed on Mar. 15, 2013.

(51) Int. Cl.
  *A61F 2/24* (2006.01)

(52) U.S. Cl.
  CPC ........... *A61F 2/2427* (2013.01); *A61F 2/2412* (2013.01); *A61F 2/2418* (2013.01); *A61F 2220/0091* (2013.01)

(58) Field of Classification Search
  CPC .. A61F 2/2403; A61F 2/2427; A61F 2/2412; A61F 2/2418; A61F 220/0091; A61F 220/0075; A61F 220/0083; A61F 2/2436; A61F 2/90; A61F 2220/0091; A61F 2220/0075; A61F 2220/0083
  USPC ....................................................... 623/2.11
  See application file for complete search history.

(56) References Cited

U.S. PATENT DOCUMENTS

| | | |
|---|---|---|
| 4,056,854 A | 11/1977 | Boretos et al. |
| 5,549,665 A | 8/1996 | Vesely et al. |
| 5,669,931 A | 9/1997 | Kupiecki et al. |
| 5,843,260 A | 12/1998 | Huskey |
| 5,846,261 A | 12/1998 | Kotula et al. |
| 6,015,431 A | 1/2000 | Thornton et al. |
| 6,016,810 A | 1/2000 | Ravenscroft |
| 6,126,686 A | 10/2000 | Badylak et al. |
| 6,168,614 B1 | 1/2001 | Andersen et al. |
| 6,287,335 B1 | 9/2001 | Drasler et al. |
| 6,378,028 B2 | 4/2002 | Inagawa et al. |

(Continued)

FOREIGN PATENT DOCUMENTS

| | | | |
|---|---|---|---|
| AU | WO 2013078497 A1 * | 6/2013 | ........... A61F 2/2418 |
| CA | 2863503 A1 | 8/2013 | |

(Continued)

OTHER PUBLICATIONS

WIPO, U.S. International Search Authority, International Search Report and Written Opinion mailed Aug. 11, 2014 in International Patent Application No. PCT/US2014/028252, 8 pages.

(Continued)

*Primary Examiner* — Melanie Tyson
*Assistant Examiner* — Erich Herbermann
(74) *Attorney, Agent, or Firm* — Inskeep IP Group, Inc.

(57) ABSTRACT

A prosthetic valve assembly that includes a stent, a tissue sleeve and an anchoring mechanism. By loading the three components of the valve assembly into a delivery catheter in a series formation, such that no two components are located within each other, the size of the delivery catheter can be reduced.

20 Claims, 3 Drawing Sheets

(56) References Cited

U.S. PATENT DOCUMENTS

| | | | |
|---|---|---|---|
| 6,402,780 | B2 | 6/2002 | Williamson, IV et al. |
| 6,425,916 | B1 | 7/2002 | Garrison et al. |
| 6,478,028 | B1 | 11/2002 | Paolitto et al. |
| 6,524,339 | B1 | 2/2003 | Adams |
| 6,592,614 | B2 | 7/2003 | Lenker et al. |
| 6,605,102 | B1 | 8/2003 | Mazzocchi et al. |
| 6,652,578 | B2 | 11/2003 | Bailey et al. |
| 6,719,781 | B1 | 4/2004 | Kim |
| 6,769,434 | B2 | 8/2004 | Liddicoat et al. |
| 6,893,457 | B2 | 5/2005 | Dong |
| 6,908,481 | B2 | 6/2005 | Cribier |
| 6,929,653 | B2 | 8/2005 | Strecter |
| 7,001,425 | B2 | 2/2006 | McCullagh et al. |
| 7,252,681 | B2 | 8/2007 | Berg et al. |
| 7,267,686 | B2 | 9/2007 | Dimatteo et al. |
| 7,329,279 | B2 | 2/2008 | Haug et al. |
| 7,445,630 | B2 | 11/2008 | Lashinski et al. |
| 8,021,420 | B2 | 9/2011 | Dolan |
| 8,157,796 | B2 | 4/2012 | Collins et al. |
| 8,663,312 | B2 | 3/2014 | Wilson et al. |
| 8,696,737 | B2 | 4/2014 | Gainor |
| 8,845,720 | B2 | 9/2014 | Conklin |
| 8,986,374 | B2 | 3/2015 | Cao et al. |
| 2002/0032481 | A1 | 3/2002 | Gabbay |
| 2002/0128703 | A1 | 9/2002 | Ravenscroft |
| 2003/0014104 | A1 | 1/2003 | Cribier |
| 2004/0024416 | A1 | 2/2004 | Yodfat et al. |
| 2004/0073293 | A1 | 4/2004 | Thompson |
| 2004/0073301 | A1 | 4/2004 | Donlon et al. |
| 2004/0093075 | A1 | 5/2004 | Kuehne |
| 2004/0220664 | A1 | 11/2004 | Chobotov |
| 2004/0260333 | A1 | 12/2004 | Dubrul et al. |
| 2005/0022674 | A1 | 2/2005 | Campbell et al. |
| 2005/0075720 | A1 | 4/2005 | Nguyen et al. |
| 2005/0137691 | A1 | 6/2005 | Salahieh et al. |
| 2005/0137702 | A1 | 6/2005 | Haug et al. |
| 2005/0222674 | A1 | 10/2005 | Paine |
| 2005/0240200 | A1 | 10/2005 | Bergheim |
| 2005/0251251 | A1 | 11/2005 | Cribier |
| 2005/0283231 | A1 | 12/2005 | Haug et al. |
| 2006/0020327 | A1 | 1/2006 | Lashinski et al. |
| 2006/0074484 | A1 | 4/2006 | Huber |
| 2006/0142848 | A1 | 6/2006 | Gabbay |
| 2006/0167468 | A1 | 7/2006 | Gabbay |
| 2006/0271166 | A1* | 11/2006 | Thill ................ A61F 2/2418 623/1.23 |
| 2007/0010876 | A1 | 1/2007 | Salahieh et al. |
| 2007/0203517 | A1 | 8/2007 | Williams et al. |
| 2008/0015671 | A1 | 1/2008 | Bonhoeffer |
| 2008/0071362 | A1 | 3/2008 | Tuval et al. |
| 2008/0195199 | A1 | 8/2008 | Kheradvar et al. |
| 2008/0300678 | A1 | 12/2008 | Eidenschink et al. |
| 2009/0076598 | A1 | 3/2009 | Salahieh et al. |
| 2009/0222076 | A1 | 9/2009 | Figulla et al. |
| 2010/0168839 | A1 | 7/2010 | Braido et al. |
| 2011/0218619 | A1 | 9/2011 | Benichou et al. |
| 2011/0264206 | A1 | 10/2011 | Tabor |
| 2011/0282439 | A1 | 11/2011 | Thill et al. |
| 2012/0065728 | A1 | 3/2012 | Gainor et al. |
| 2012/0209370 | A1 | 8/2012 | Thill et al. |
| 2013/0144383 | A1 | 6/2013 | Thill et al. |
| 2013/0204357 | A1 | 8/2013 | Thill et al. |
| 2013/0204360 | A1 | 8/2013 | Gainor |
| 2013/0282098 | A1 | 10/2013 | Thill et al. |
| 2014/0155996 | A1 | 6/2014 | Wilson et al. |

FOREIGN PATENT DOCUMENTS

| | | |
|---|---|---|
| CN | 101991478 B | 4/2013 |
| DE | 102005052628 A1 | 5/2007 |
| EP | 1 915 105 A2 | 4/2008 |
| EP | 2 809 272 A1 | 12/2014 |
| EP | 2 967 861 A1 | 1/2016 |
| JP | H0611637 A | 1/1994 |
| JP | H1029161 A | 2/1998 |
| JP | 2000-291883 A | 10/2000 |
| JP | 2002-182095 A | 6/2002 |
| JP | 2002-228903 A | 8/2002 |
| JP | 2002-328317 A | 11/2002 |
| JP | 2002-537943 A | 11/2002 |
| JP | 2003-506133 A | 2/2003 |
| JP | 2003-098443 A | 4/2003 |
| JP | 2004-503327 A | 2/2004 |
| JP | 2007-237136 A | 9/2007 |
| JP | 4093401 B2 | 6/2008 |
| JP | 4549278 B2 | 9/2010 |
| JP | 5289049 B2 | 9/2013 |
| JP | 2014-000472 A | 1/2014 |
| JP | 2015-509033 A | 3/2015 |
| JP | 5749231 B2 | 7/2015 |
| JP | 2016-028783 A | 3/2016 |
| JP | 2016-064147 A | 4/2016 |
| WO | 97/27799 A1 | 8/1997 |
| WO | 97/30659 A1 | 8/1997 |
| WO | 99/15112 A1 | 4/1999 |
| WO | 00/53120 A1 | 9/2000 |
| WO | 02/05729 A2 | 1/2002 |
| WO | 03/092554 A1 | 11/2003 |
| WO | 2004/082528 A3 | 9/2004 |
| WO | 2005/058408 A1 | 6/2005 |
| WO | 2006/036690 A1 | 4/2006 |
| WO | 2006/083763 A1 | 8/2006 |
| WO | 2006/128193 A2 | 11/2006 |
| WO | 2007/051620 A1 | 5/2007 |
| WO | 2008/072838 A1 | 6/2008 |
| WO | 2008/097589 A1 | 8/2008 |
| WO | WO2009/153768 A1 | 12/2009 |
| WO | 2011/143263 A2 | 11/2011 |
| WO | 2013/116785 A1 | 8/2013 |
| WO | 2014/144020 A1 | 9/2014 |

OTHER PUBLICATIONS

State Intellectual Property Office, P.R. China, Office Action and Search Report mailed Sep. 28, 2015 with English translation in Chinese Patent Application No. CN201380018393, 20 pages.
United States Patent and Trademark Office, Notice of Allowance mailed May 13, 2016 in U.S. Appl. No. 14/635,951, 5 pages.
United States Patent and Trademark Office, Notice of Allowance mailed May 11, 2016 in U.S. Appl. No. 13/834,135, 7 pages.
United States Patent and Trademark Office, Final Office Action mailed Jan. 15, 2016 in U.S. Appl. No. 14/635,951, 6 pages.
United States Patent and Trademark Office, Final Office Action mailed Jan. 15, 2016 in U.S. Appl. No. 13/834,135, 8 pages.
United States Patent and Trademark Office, Final Office Action mailed Nov. 17, 2008 in U.S. Appl. No. 11/443,814, 10 pages.
United States Patent and Trademark Office, Office Action mailed Sep. 11, 2015 in U.S. Appl. No. 14/635,951, 17 pages.
United States Patent and Trademark Office, Office Action mailed Jul. 7, 2015 in U.S. Appl. No. 13/834,135, 9 pages.
Japan Patent Office, Official Action dated Dec. 11, 2014 in Japanese Patent Application Serial No. JP2012-180576 with English translation, 7 pages.
United States Patent and Trademark Office, Notice of Allowance mailed Dec. 8, 2014 in U.S. Appl. No. 11/443,814, 7 pages.
United States Patent and Trademark Office, Final Office Action mailed Sep. 18, 2014 in U.S. Appl. No. 13/651,249, 8 pages.
United States Patent and Trademark Office, Office Action mailed Sep. 12, 2014 in U.S. Appl. No. 13/895,230, 8 pages.
United States Patent and Trademark Office, Office Action mailed Sep. 12, 2014 in U.S. Appl. No. 13/458,023, 9 pages.
United States Patent and Trademark Office, Final Office Action mailed Apr. 24, 2014 in U.S. Appl. No. 13/104,866, 7 pages.
United States Patent and Trademark Office, Office Action mailed Apr. 11, 2014 in U.S. Appl. No. 13/895,230, 12 pages.
United States Patent and Trademark Office, Final Office Action mailed Mar. 31, 2014 in U.S. Appl. No. 11/443,814, 9 pages.
United States Patent and Trademark Office, Office Action mailed Mar. 28, 2014 in U.S. Appl. No. 13/192,375, 8 pages.

(56) References Cited

OTHER PUBLICATIONS

United States Patent and Trademark Office, Office Action mailed Mar. 21, 2014 in U.S. Appl. No. 13/458,023, 8 pages.
Japan Patent Office, Official Action mailed Mar. 3, 2014 in Japanese Patent Application Serial No. JP2012-180576 with English translation, 9 pages.
United States Patent and Trademark Office, Office Action mailed Feb. 27, 2014 in U.S. Appl. No. 13/651,249, 7 pages.
European Patent Office, Examination Report dated Feb. 17, 2014 in European Patent Application No. EP06771666, 5 pages.
United States Patent and Trademark Office, Office Action mailed Jan. 5, 2015 in U.S. Appl. No. 13/651,249, 14 pages.
United States Patent and Trademark Office, Final Office Action mailed Oct. 8, 2013 in U.S. Appl. No. 13/192,375, 7 pages.
United States Patent and Trademark Office, Office Action mailed Aug. 26, 2013 in U.S. Appl. No. 11/443,814, 8 pages.
United States Patent and Trademark Office, Final Office Action mailed Jul. 24, 2013 in U.S. Appl. No. 13/104,866, 5 pages.
United States Patent and Trademark Office, Office Action mailed Jul. 3, 2013 in U.S. Appl. No. 13/192,375, 9 pages.
European Patent Office, Supplementary European Search Report dated Jun. 13, 2013 in European Patent Application No. EP06771666, 7 pages.
United States Patent and Trademark Office, Office Action mailed Jun. 12, 2013 in U.S. Appl. No. 13/458,023, 7 pages.
Japan Patent Office, Official Action dated May 29, 2013 in Japanese Patent Application Serial No. JP2008-513838, 3 pages.
European Patent Office, Examination Report dated Feb. 14, 2013 in European Patent Application No. 06771666.2-1651, 3 pages.
Japanese Patent Office, Office Action mailed Jan. 28, 2013 with English translation in Japanese Patent Application No. 2008-513838, 11 pages.
WIPO, International Preliminary Report on Patentability for International Application No. PCT/US2006/021021 issued on Nov. 30, 2007, 6 pages.
United States Patent and Trademark Office, Office Action mailed Dec. 20, 2012 in U.S. Appl. No. 13/104,866, 4 pages.
Canadian Intellectual Property Office, Office Action mailed Dec. 6, 2012 in Canadian Patent Application No. 2,613,958, 3 pages.
United States Patent and Trademark Office, Office Action mailed Nov. 14, 2012 in U.S. Appl. No. 11/443,814, 10 pages.
United States Patent and Trademark Office, Office Action mailed Nov. 13, 2012 in U.S. Appl. No. 13/458,023, 7 pages.
IP Australia, Examiner's Report mailed Jul. 16, 2012 in Australian Patent Application No. 2011265440, 3 pages.
Chinese Patent Office, Office Action mailed Jun. 1, 2012 in Chinese Patent Application No. 201010533068.8, 4 pages.
Japanese Patent Office, Office Action mailed May 2, 2012 in Japanese Patent Application No. 2008-513838, 4 pages.
Japanese Patent Office, Office Action mailed Sep. 28, 2011 in Japanese Patent Application No. JP2008-513838, 7 pages.
IP Australia, Notice of Acceptance mailed Sep. 15, 2011 in Australian Patent Application No. AU2006251938, 3 pages.
WIPO, U.S International Search Authority, International Search Report and Written Opinion mailed Aug. 17, 2011 in International Patent Application No. PCT/US 11/35983, 7 pages.
State Intellectual Property Office, P.R. China, First Office Action mailed Nov. 27, 2009 in Chinese Patent Application No. CN201010533068.8, 4 pages.

IP Australia, Examiner's Report mailed Apr. 18, 2011 in Australian Patent Application No. AU2006251938, 2 pages.
United States Patent and Trademark Office, Final Office Action mailed Dec. 14, 2010 in U.S. Appl. No. 11/443,814, 10 pages.
State Intellectual Property Office, P.R. China, Notification to go Through Formalities of Registration mailed Aug. 3, 2010 in Chinese Patent Application No. 200680027512.0 with English translation, 5 pages.
United States Patent and Trademark Office, Final Office Action mailed Jul. 22, 2010 in U.S. Appl. No. 11/443,814, 9 pages.
United States Patent and Trademark Office, Office Action mailed Dec. 29, 2009 in U.S. Appl. No. 11/443,814, 7 pages.
State Intellectual Property Office, P.R. China, Examiner's Report mailed Nov. 27, 2009 in Chinese Patent Application No. CN200680027512.0, 6 pages.
United States Patent and Trademark Office, Office Action mailed Apr. 17, 2009 in U.S. Appl. No. 11/443,814, 7 pages.
WIPO, U.S International Preliminary Examining Authority, International Preliminary Report on Patentability mailed Sep. 15, 2015 in International Patent Application No. PCT/US2014/028252, 6 pages.
United States Patent and Trademark Office, Office Action mailed Mar. 18, 2008 in U.S. Appl. No. 11/443,814, 10 pages.
WIPO, U.S. International Preliminary Examining Authority, International Preliminary Report on Patentability mailed Nov. 30, 2007 in International Patent Application No. PCT/US2006/021021, 7 pages.
WIPO, U.S. International Search Authority, International Search Report and Written Opinion mailed Sep. 5, 2007 in International Patent Application No. PCT/US2006/021021, 10 pages.
WIPO, U.S. International Search Authority, International Search Report and Written Opinion mailed May 13, 2013 in International Patent Application No. PCT/US2013/024514, 10 pages.
WIPO, U.S International Preliminary Examining Authority, International Preliminary Report on Patentability mailed Aug. 5, 2014 in International Patent Application No. PCT/US2013/024514, 8 pages.
United States Patent and Trademark Office, Office Action mailed Dec. 20, 2012 in U.S. Appl. No. 13/104,866, 7 pages.
IP Australia, Examiner's Report mailed Dec. 12, 2014 in Australian Patent Application No. 2013213684, 7 pages.
State Intellectual Property Office, P.R. China, Examiner's Report mailed Jul. 29, 2011 in Chinese Patent Application No. CN201010533068.8, 4 pages.
State Intellectual Property Office, P.R. China, Examiner's Report mailed Apr. 27, 2011 in Chinese Patent Application No. CN201010533068.8, 4 pages.
European Patent Office, Examination Report dated Mar. 17, 2015 in European Patent Application No. EP06771666.2, 5 pages.
State Intellectual Property Office, P.R. China, Examiner's Report mailed Sep. 28, 2015 in Chinese Patent Application No. CN201380018393.2, 13 pages.
State Intellectual Property Office, P.R. China, Search Report in Chinese Patent Application No. CN201380018393.2 mailed Feb. 1, 2013 , 2 pages.
European Patent Office, Extended European Search Report dated Aug. 28, 2015 in European Patent Application No. EP13743728.1, 9 pages.
United States Patent and Trademark Office, Final Office Action mailed Jul. 22, 2010 in U.S. Appl. No. 11/443,814, 8 pages.
United States Patent and Trademark Office, Office Action mailed Dec. 29, 2009 in U.S. Appl. No. 11/443,814, 14 pages.

\* cited by examiner

LOW-PROFILE PROSTHETIC VALVE STRUCTURE

RELATED APPLICATIONS

This application claims benefit of and priority to U.S. Provisional Application Ser. No. 61/800,153 filed Mar. 15, 2013 entitled Low-Profile Prosthetic Valve Structure, which is hereby incorporated herein by reference in its entirety.

BACKGROUND OF THE INVENTION

Replacing heart valves with prosthetic valves was, until recently, a complicated surgical procedure that involved cutting open the chest, establishing blood flow through a blood pump, stopping the heart, etc. This complicated procedure, even when performed perfectly, required extensive recovery time due to the invasiveness and damage done to access the implantation site. Additionally, the risk of infection or other complications is extremely high.

Numerous advancements have been made to develop prosthetic valves that can be implanted percutaneously, using a catheter to snake the prosthetic valve through the vasculature to the implantation site. If successful, the recovery time is greatly minimized relative to conventional open-heart surgery.

A designer of a percutaneously-delivered prosthetic valve is faced with numerous challenges, however. First and foremost is designing a prosthetic valve that can be compressed enough to be inserted into a catheter small enough to be navigated to the valve site through the vasculature. Other challenges include anchoring the valve at the valve site so the valve does not migrate after release; including a support structure for the valve that is robust enough to push the native, often calcified valve out of the way and prevent it from later interfering with the function of the new valve; ensuring that the new valve allows proper flow in a desired direction and effectively stops flow in the opposite direction; ensuring that no blood flows around the sides of the implanted device (this is known as perivalvular leakage); designing a prosthetic valve device that does not fail due to fatigue after hundreds of thousands of cycles of leaflet function; designing a valve that meets all of these criteria and can still be manufactured economically; and the list goes on.

These prosthetic valves, and their respective delivery catheters, are designed to replace a particular native valve, such as the aortic valve, for example. Percutaneous navigation to a valve is easiest, and least traumatic to the patient, when a smaller catheter is used. Smaller catheters, however, present challenges when designing effective prosthetic valves that can be compressed enough to fit, and slide, within the lumen of a small catheter, such as a 16 Fr or even a 14 Fr catheter. Significant strides have been made in recent years in designing prosthetic valves that have reduced profiles when in a catheter-loaded configuration. For example, the devices described in U.S. Patent Publication Number 2006/0271166 to Thill et al., the contents of which are incorporated by reference herein, can assume an elongated, unfolded configuration when loaded into a catheter and, when released from the catheter at a target site, resume a folded configuration. The present invention is directed to taking this innovative concept and presenting additional ways that the loaded configuration could present an even lower profile.

OBJECTS AND SUMMARY OF THE INVENTION

One aspect of the invention is directed to a prosthetic valve device that presents a low profile in a catheter-loaded configuration.

Another aspect of the invention is directed to a prosthetic valve device that is sized to replace an aortic valve and capable of being delivered using a small, flexible catheter.

Another aspect of the invention is directed to a prosthetic valve device that comprises two components are connected but positioned in series (spaced apart axially) in a delivery catheter to reduce the size of the delivery catheter required.

One aspect of the invention provides a device for replacing a native valve comprising: a stent; a tissue sleeve; and, an anchoring mechanism usable to secure said tissue sleeve within said stent; wherein, in a configuration inside a delivery catheter, said anchoring mechanism is not located within said stent; and wherein, in a deployed configuration, said tissue sleeve is located within said stent.

Another aspect of the invention provides prosthetic valve device that comprises a braided anchoring mechanism connected at a proximal end to a wireform.

Another aspect of the invention provides an implantable device that includes a support structure having an extended configuration and a folded configuration, the support structure having a first end, a second end and a preformed fold between said first end and said second end, wherein said preformed fold at least assists in inverting said first portion into said second portion when said support structure is released from a delivery device, and a prosthetic valve structure including a hinged end hingedly attached to said support structure first end, thereby allowing said support structure first portion to invert into said support structure second portion without inverting said prosthetic valve structure.

Another aspect of the invention provides an implantable prosthetic valve structure with a support structure that has a folded configuration in which the prosthetic valve structure extends, at least partially, into said support structure.

Another aspect of the invention provide a prosthetic valve device that includes a support structure that has inwardly curved sidewalls when it is in a folded configuration.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
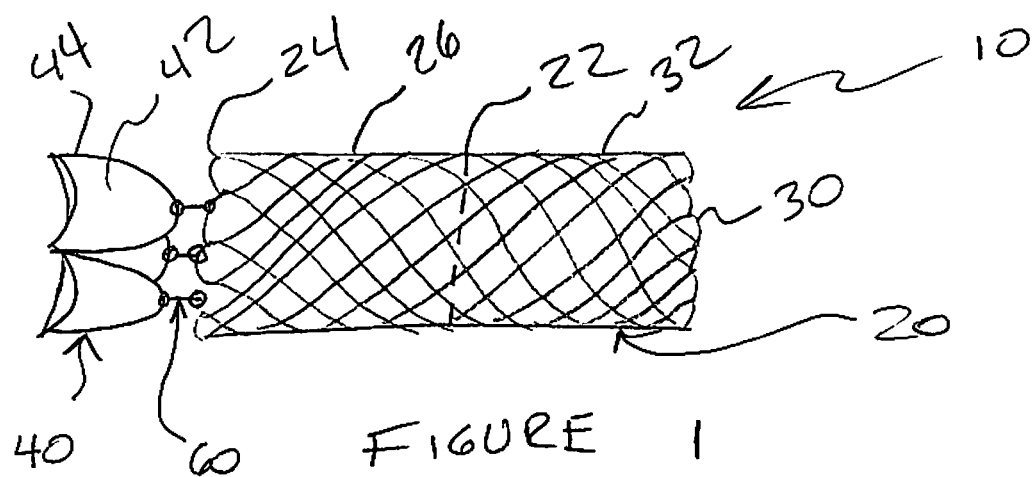
FIG. 1 is an elevation of an embodiment of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring first to FIG. 1 there is shown a device 10 of the invention. Device 10 generally includes a support structure 20, a valve assembly 40, and a connection 60 between the support structure 20 and the valve assembly 40. FIG. 1 shows the device 10 in an elongate configuration prior to being compressed in order to fit within the lumen of a delivery catheter. It can be seen that the support structure 20, the valve assembly 40, and the connection mechanism 60 are all linearly arranged along a longitudinal axis in a series configuration, with no overlapping of components.

With regard to the support structure, a dotted line 22 represents a preformed fold created in the support structure 20 that at least partially causes the device 10 to fold inwardly on itself when released from a delivery catheter. The support structure 20 can be described as having a first end 24, a first portion 26 between the first end 24 and the preformed fold 22, a second end 30, and second portion 32 between the second end 30 and the preformed fold 22.

The valve assembly 40 includes tissue valve 42 attached to a wireform 44. The wireform 44 gives structural integrity to the tissue valve 42.

The connection 60 between the valve assembly 40 and the support structure 20 is described in more detail below.

Figure 2:
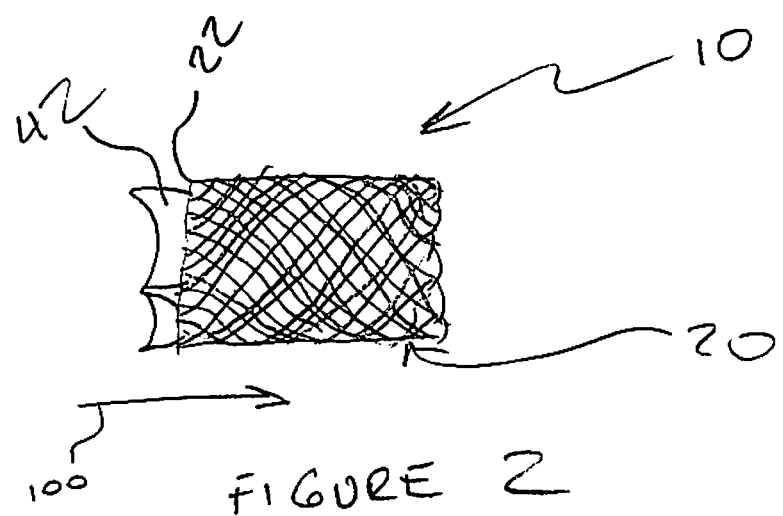
FIG. 2 is an elevation of an embodiment of the invention in a folded configuration.

FIG. 2 shows the device 10 of FIG. 1 in a fully expanded, delivered configuration. The device 10 has folded inwardly on itself such that the fold 22 is now defining the proximal end of the support structure 20. As the device 10 folded, the wireform 40, which contains a tissue valve 42, is drawn into the support structure 20. Because the first portion 26 is now inverted, in other words, it is inside-out in comparison to its prefolded configuration of FIG. 1, the connection mechanism 60 must hinge or pivot in order to maintain the orientation of the valve assembly 40. Because the connection mechanism 60 hinges, when the first portion 24 inverts into the second portion 32, the valve assembly 40 moves only linearly (axially) into the support structure 20, as shown by the arrow 100 in FIG. 2. Thus, only one preformed fold 22 is needed in the support structure 20 to allow the valve assembly 40 to maintain its orientation while moving axially.

Figure 3:
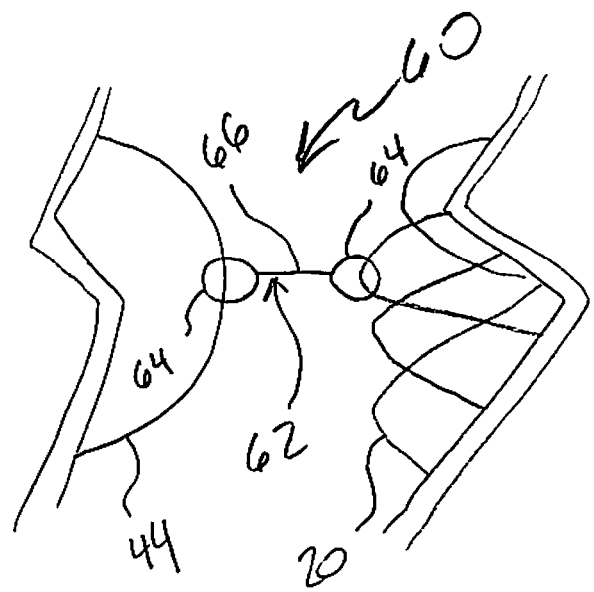
FIG. 3 is a partial view of an embodiment of the invention.

FIG. 3 shows an embodiment of a connection mechanism 60. The connection mechanism 60 may be a link 62 having two ring connectors 64 separated by a spacer 66. The spacer 66 is sized to ensure that, in the elongated configuration, the connection mechanism 60 adequately separates the support structure 20 from the valve assembly 40. The connection mechanism 60 may be constructed of a variety of biocompatible material such as an alloy, including but not limited to stainless steel and Nitinol, or may be a polymer or other suitable non-metallic material.

Figure 4:
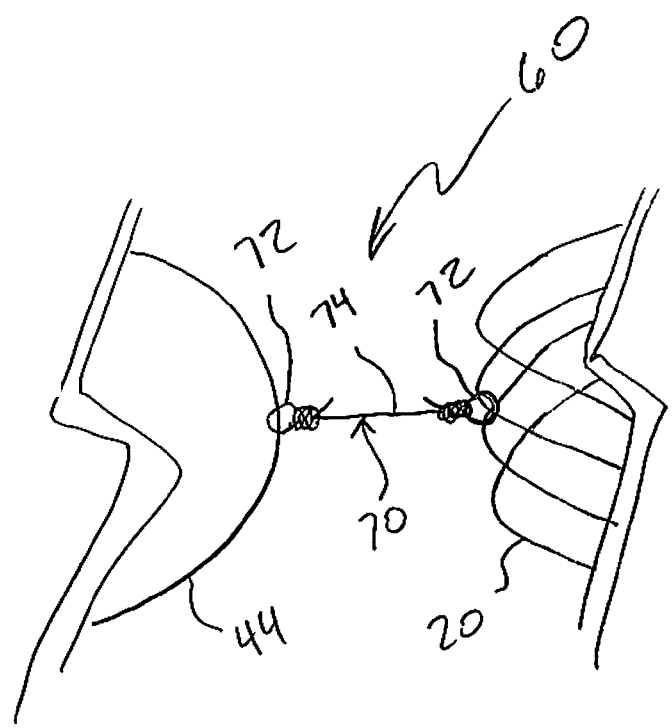
FIG. 4 is a partial view of an embodiment of the invention.

FIG. 4 shows another embodiment of a connection mechanism 60. This connection mechanism 60 may be a tether 70 having ends 72 that are tied to the wireform 44 of the valve assembly 40 and to the support structure 20. The tether may be constructed of any suture material or may be a wire having suitable flexibility to be tied in a knot. The length of the tether 70 between the tied ends 72 constitutes a spacer 74 that is sized to ensure adequate separation of the support structure 20 from the valve assembly 40 in the elongated configuration of FIG. 1.

Figure 5:
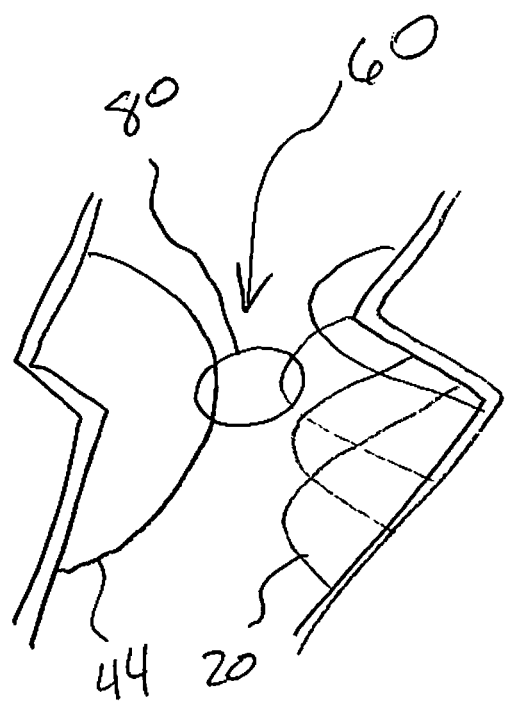
FIG. 5 is a partial view of an embodiment of the invention.

FIG. 5 shows an embodiment of a connection mechanism 60 that is a single loop 80. The loop 80 extends around the wireform 44 and a strand of the support structure 20. The loop 80 is sized to ensure adequate separation of the support structure 20 from the valve assembly 40 in the elongated configuration of FIG. 1.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An implantable device comprising:
   a support structure having an extended configuration and a folded configuration and including:
      a first end;
      a second end;
      a single preformed fold between said first end and said second end;
      a first portion between said first end and said preformed fold;
      a second portion between said second end and said preformed fold;
   wherein said preformed fold at least assists in inverting said first portion into said second portion when said support structure is released from a delivery device;
   a prosthetic valve structure;
   at least one connector hingedly connecting the prosthetic valve structure to the support structure first end such that the at least one connector rotates relative to said support structure first end to allow said support structure first portion to invert into said support structure second portion without inverting said prosthetic valve structure.

2. The implantable device of claim 1 wherein said at least one connector comprises a hinge.

3. The implantable device of claim 1 wherein said at least one connector comprises a link.

4. The implantable device of claim 3 wherein said link comprises two ring connectors separated by a spacer.

5. The implantable device of claim 1 wherein, in said extended configuration, said connector separates said support structure from said valve structure.

6. The implantable device of claim 1 wherein said at least one connector comprises a tether.

7. The implantable device of claim 1 wherein inverting said first portion into said second portion when said support structure is released changes said support structure from said extended configuration to said folded configuration.

8. An implantable device comprising:
   a support structure having a single preformed fold, and a first portion and a second portion separated from said first portion by said preformed fold;
   a valve assembly;
   a connector connecting said valve assembly to said first portion of said support structure;
   wherein said implantable device has a first configuration and a second configuration;
   wherein in said first configuration, said support structure is unfolded and said support structure, said valve assembly, and said connector are axially arranged;
   wherein in said second configuration, said connector rotates relative to said first portion of said support structure while said first portion is inverted into said second portion and said valve assembly is drawn at least partially into said first portion by said connector.

9. The implantable device of claim 8 wherein said connector pivots such that said when said first portion inverts, said valve assembly does not invert.

10. The implantable device of claim 8 wherein said connector comprises a hinge.

11. The implantable device of claim 8 wherein said connector comprises a link.

12. The implantable device of claim 11 wherein said link comprises two ring connectors separated by a spacer.

13. The implantable device of claim 8 wherein, in said elongated configuration, said connector separates said support structure from said valve assembly.

14. The implantable device of claim 8 wherein said connector comprises a tether.

15. The implantable device of claim 14 wherein said tether comprises a first end tied to the support structure and a second end tied to the valve assembly.

16. The implantable device of claim 8 wherein said connector comprises a loop.

17. A method of delivering an implantable device comprising:
    arranging a first component with a single preformed circumferential fold, a connector, and a second component axially in a delivery catheter, said connector connecting said first component and said second component such that said first and second components do not overlap;
    releasing said first component, said connector, and said second component at a target site from said catheter;
    allowing said first component to fold into itself along said circumferential fold while said connector pivots, thereby drawing said second component axially toward said first component.

18. The method of claim 17 wherein allowing said first component to fold into itself comprises creating a preformed fold in said first component prior to arranging, and unfolding said preformed fold during said arranging step such that said preformed fold causes said first component to fold into itself when released.

19. The method of claim 17 wherein arranging a first component, a connector and a second component axially in a delivery catheter comprises arranging a support structure, a connector, and a valve assembly in a delivery catheter.

20. The method of claim 17 wherein arranging a first component, a connector, and a second component axially in a delivery catheter, said connector connecting said first component and said second component such that said first and second components do not overlap, comprises arranging said first component, said connector, and said second component axially in said delivery catheter such that said first component and said second component are spaced apart from each other.

* * * * *